(12) United States Patent
Lagrimini et al.

(10) Patent No.: US 6,278,041 B1
(45) Date of Patent: Aug. 21, 2001

(54) PEROXIDASE GENE SEQUENCES

(75) Inventors: Lawrence Mark Lagrimini, Apex; Nalini M Desai, Chapel Hill, both of NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 09/365,150

(22) Filed: Jul. 30, 1999

(51) Int. Cl.[7] .............................. A01H 1/00; C07H 21/04; C07K 14/415; C12N 5/14; C12N 9/00
(52) U.S. Cl. .................. 800/279; 800/278; 800/301; 435/69.1; 435/410; 435/418; 435/419; 435/252.3; 435/320.1; 435/183; 530/370; 536/23.1; 536/23.6; 536/24.1
(58) Field of Search ..................... 800/278, 279, 800/301; 435/69.1, 410, 418, 419, 252.3, 320.1, 183; 530/370; 536/23.1, 23.6, 24.1

(56) References Cited

U.S. PATENT DOCUMENTS 5,625,136  4/1997  Koziel et al. .................. 800/205
6,002,068  12/1999  Privalle et al. ................ 800/279

OTHER PUBLICATIONS

Lagrimini et al., Plant Cell 2: 7–18 (1990).
Lagrimini et al., Plant Phsyiology 96: 577–583 (1991).
Lagrimini et al., J. Amer. Soc. Hort. Sci. 117(6): 1012–1016 (1992).
Lagrimini et al., HortScience 28(3): 218–221 (1993).
Genbank Accession No. J02979 Apr. 27, 1993.

Primary Examiner—Phuong T. Bui
(74) Attorney, Agent, or Firm—J. Timothy Meigs

(57) ABSTRACT

A anionic peroxidase gene sequence is isolated from *Nicotiana tomentisiformis*. In addition, synthetic *Nicotiana tomentisiformis* and *Nicotiana sylvestris* peroxidase gene sequences are optimized for expression in plants. The peroxidase gene sequences may be expressed in transgenic plants to control insects.

10 Claims, No Drawings ated by the plant. Peroxidases are critical in the biosynthesis of plant cell walls. Peroxidases promote the peroxidative polymerization of the monolignols coniferyl, r-coumaryl, and sinapyl alcohol into lignin (Greisbach, In: The Biochemistry of Plants, Ed. Conn, Academic, New York pp. 457–480 (1991)). Different plant species have varying ratios of the monolignol species assembled in a semi-random fashion (Hwang et al., Carbohydrate Polymers 14:77–88 (1991)). Lignification serves to strengthen and reinforce cell walls. The overall result is a toughening of the plant tissue.

SEQUENCE LISTING

<160> NUMBER OF SEQ ID NOS: 6

<210> SEQ ID NO 1
<211> LENGTH: 975
<212> TYPE: DNA
<213> ORGANISM: Nicotiana tomentosiformis
<220> FEATURE:
<221> NAME/KEY: CDS
<222> LOCATION: (1)..(972)

<400> SEQUENCE: 1

| atg | tct | ttt | tta | aga | ttt | gtt | ggt | aca | att | ctt | ttc | ttg | gtt | gca | att | 48 |
|-----|-----|-----|-----|-----|-----|-----|-----|-----|-----|-----|-----|-----|-----|-----|-----|----|
| Met | Ser | Phe | Leu | Arg | Phe | Val | Gly | Thr | Ile | Leu | Phe | Leu | Val | Ala | Ile | |
| 1 | | | | 5 | | | | | 10 | | | | | 15 | | |

| ttt | gca | gca | tca | aat | gct | caa | tta | agt | gca | aca | ttt | tac | gat | agc | act | 96 |
|-----|-----|-----|-----|-----|-----|-----|-----|-----|-----|-----|-----|-----|-----|-----|-----|----|
| Phe | Ala | Ala | Ser | Asn | Ala | Gln | Leu | Ser | Ala | Thr | Phe | Tyr | Asp | Ser | Thr | |
| | | | 20 | | | | | 25 | | | | | 30 | | | |

| tgt | cct | aat | gtt | aca | agt | att | gta | cgt | ggt | gtt | atg | gat | caa | agg | caa | 144 |
|-----|-----|-----|-----|-----|-----|-----|-----|-----|-----|-----|-----|-----|-----|-----|-----|-----|
| Cys | Pro | Asn | Val | Thr | Ser | Ile | Val | Arg | Gly | Val | Met | Asp | Gln | Arg | Gln | |
| | | 35 | | | | | 40 | | | | | 45 | | | | |

| cgt | act | gat | gct | cga | gct | ggt | gct | aaa | att | att | cgt | ctt | cat | ttc | cac | 192 |
|-----|-----|-----|-----|-----|-----|-----|-----|-----|-----|-----|-----|-----|-----|-----|-----|-----|
| Arg | Thr | Asp | Ala | Arg | Ala | Gly | Ala | Lys | Ile | Ile | Arg | Leu | His | Phe | His | |
| 50 | | | | | 55 | | | | | 60 | | | | | | |

| gat | tgc | ttt | gtc | aat | ggt | tgt | gat | gga | tcc | att | tta | tta | gac | aca | gat | 240 |
|-----|-----|-----|-----|-----|-----|-----|-----|-----|-----|-----|-----|-----|-----|-----|-----|-----|
| Asp | Cys | Phe | Val | Asn | Gly | Cys | Asp | Gly | Ser | Ile | Leu | Leu | Asp | Thr | Asp | |
| 65 | | | | | 70 | | | | | 75 | | | | | 80 | |

| ggg | act | caa | act | gag | aaa | gat | gca | gct | cct | aat | gta | ggt | gcg | gga | gga | 288 |
|-----|-----|-----|-----|-----|-----|-----|-----|-----|-----|-----|-----|-----|-----|-----|-----|-----|
| Gly | Thr | Gln | Thr | Glu | Lys | Asp | Ala | Ala | Pro | Asn | Val | Gly | Ala | Gly | Gly | |
| | | | | 85 | | | | | 90 | | | | | 95 | | |

| ttt | gat | att | gtt | gat | gat | att | aaa | act | gca | tta | gag | aat | gta | tgc | cct | 336 |
|-----|-----|-----|-----|-----|-----|-----|-----|-----|-----|-----|-----|-----|-----|-----|-----|-----|
| Phe | Asp | Ile | Val | Asp | Asp | Ile | Lys | Thr | Ala | Leu | Glu | Asn | Val | Cys | Pro | |
| | | | 100 | | | | | 105 | | | | | 110 | | | |

| ggt | gtt | gta | tct | tgt | gca | gat | att | tta | tcc | ctt | gca | tct | gaa | att | gga | 384 |
|-----|-----|-----|-----|-----|-----|-----|-----|-----|-----|-----|-----|-----|-----|-----|-----|-----|
| Gly | Val | Val | Ser | Cys | Ala | Asp | Ile | Leu | Ser | Leu | Ala | Ser | Glu | Ile | Gly | |
| | | 115 | | | | | 120 | | | | | 125 | | | | |

| gtt | gcc | ttg | gcg | gaa | ggt | ccg | tca | tgg | caa | gta | ctt | ttt | ggc | aga | aaa | 432 |
|-----|-----|-----|-----|-----|-----|-----|-----|-----|-----|-----|-----|-----|-----|-----|-----|-----|
| Val | Ala | Leu | Ala | Glu | Gly | Pro | Ser | Trp | Gln | Val | Leu | Phe | Gly | Arg | Lys | |
| | 130 | | | | | 135 | | | | | 140 | | | | | |

| aac | agc | tta | aca | gca | aac | cga | tct | gaa | gct | aat | agt | gat | atc | ccc | agc | 480 |
|-----|-----|-----|-----|-----|-----|-----|-----|-----|-----|-----|-----|-----|-----|-----|-----|-----|
| Asn | Ser | Leu | Thr | Ala | Asn | Arg | Ser | Glu | Ala | Asn | Ser | Asp | Ile | Pro | Ser | |
| 145 | | | | | 150 | | | | | 155 | | | | | 160 | |

```
ccc ttt gaa acc cct gct gta atg aca cca cta ttc acc aac aag gga    528
Pro Phe Glu Thr Pro Ala Val Met Thr Pro Leu Phe Thr Asn Lys Gly
                165                 170                 175 atg gat tta act gat ctt gtt gct caa tca ggt gca cat aca ttt gga    576
Met Asp Leu Thr Asp Leu Val Ala Gln Ser Gly Ala His Thr Phe Gly
            180                 185                 190 aga gca aga tgt ggt act ttt gaa caa cgt ctc ttt aac ttc agt ggc    624
Arg Ala Arg Cys Gly Thr Phe Glu Gln Arg Leu Phe Asn Phe Ser Gly
        195                 200                 205 agt ggt aac cct gat cct acc gta gac gct aca ttt tta caa aca tta    672
Ser Gly Asn Pro Asp Pro Thr Val Asp Ala Thr Phe Leu Gln Thr Leu
    210                 215                 220 caa gga att tgt cct caa ggt gga aat aat ggc aat act ttt aca aat    720
Gln Gly Ile Cys Pro Gln Gly Gly Asn Asn Gly Asn Thr Phe Thr Asn
225                 230                 235                 240 ctt gat ata tca act cct aat gac ttt gat aat gac tat ttc aca aac    768
Leu Asp Ile Ser Thr Pro Asn Asp Phe Asp Asn Asp Tyr Phe Thr Asn
                245                 250                 255 ctt caa aat aat caa ggg ctc ctt caa act gat caa gag ttg ttt tca    816
Leu Gln Asn Asn Gln Gly Leu Leu Gln Thr Asp Gln Glu Leu Phe Ser
            260                 265                 270 aca tct gga tct gct aca att gca ata gtt aat cgt tat gct ggt agc    864
Thr Ser Gly Ser Ala Thr Ile Ala Ile Val Asn Arg Tyr Ala Gly Ser
        275                 280                 285 caa act cag ttt ttt gat gat ttt gtt agc tct atg att aaa ttg ggt    912
Gln Thr Gln Phe Phe Asp Asp Phe Val Ser Ser Met Ile Lys Leu Gly
    290                 295                 300 aat ata agt cca tta act ggt act aat gga gaa att agg aca gat tgc    960
Asn Ile Ser Pro Leu Thr Gly Thr Asn Gly Glu Ile Arg Thr Asp Cys
305                 310                 315                 320 aag agg gtt aat tag                                                975
Lys Arg Val Asn <210> SEQ ID NO 2
<211> LENGTH: 324
<212> TYPE: PRT
<213> ORGANISM: Nicotiana tomentosiformis

<400> SEQUENCE: 2

Met Ser Phe Leu Arg Phe Val Gly Thr Ile Leu Phe Leu Val Ala Ile
 1               5                  10                  15

Phe Ala Ala Ser Asn Ala Gln Leu Ser Ala Thr Phe Tyr Asp Ser Thr
                20                  25                  30

Cys Pro Asn Val Thr Ser Ile Val Arg Gly Val Met Asp Gln Arg Gln
            35                  40                  45

Arg Thr Asp Ala Arg Ala Gly Ala Lys Ile Ile Arg Leu His Phe His
        50                  55                  60

Asp Cys Phe Val Asn Gly Cys Asp Gly Ser Ile Leu Leu Asp Thr Asp
 65                 70                  75                  80

Gly Thr Gln Thr Glu Lys Asp Ala Ala Pro Asn Val Gly Ala Gly Gly
                85                  90                  95

Phe Asp Ile Val Asp Asp Ile Lys Thr Ala Leu Glu Asn Val Cys Pro
            100                 105                 110

Gly Val Val Ser Cys Ala Asp Ile Leu Ser Leu Ala Ser Glu Ile Gly
        115                 120                 125

Val Ala Leu Ala Glu Gly Pro Ser Trp Gln Val Leu Phe Gly Arg Lys
    130                 135                 140
```

```
Asn Ser Leu Thr Ala Asn Arg Ser Glu Ala Asn Ser Asp Ile Pro Ser
145                 150                 155                 160

Pro Phe Glu Thr Pro Ala Val Met Thr Pro Leu Phe Thr Asn Lys Gly
            165                 170                 175

Met Asp Leu Thr Asp Leu Val Ala Gln Ser Gly Ala His Thr Phe Gly
            180                 185                 190

Arg Ala Arg Cys Gly Thr Phe Glu Gln Arg Leu Phe Asn Phe Ser Gly
            195                 200                 205

Ser Gly Asn Pro Asp Pro Thr Val Asp Ala Thr Phe Leu Gln Thr Leu
            210                 215                 220

Gln Gly Ile Cys Pro Gln Gly Gly Asn Gly Asn Thr Phe Thr Asn
225                 230                 235                 240

Leu Asp Ile Ser Thr Pro Asn Asp Phe Asp Asn Asp Tyr Phe Thr Asn
                245                 250                 255

Leu Gln Asn Asn Gln Gly Leu Leu Gln Thr Asp Gln Glu Leu Phe Ser
                260                 265                 270

Thr Ser Gly Ser Ala Thr Ile Ala Ile Val Asn Arg Tyr Ala Gly Ser
            275                 280                 285

Gln Thr Gln Phe Phe Asp Asp Phe Val Ser Ser Met Ile Lys Leu Gly
290                 295                 300

Asn Ile Ser Pro Leu Thr Gly Thr Asn Gly Glu Ile Arg Thr Asp Cys
305                 310                 315                 320

Lys Arg Val Asn

<210> SEQ ID NO 3
<211> LENGTH: 975
<212> TYPE: DNA
<213> ORGANISM: Artificial Sequence
<220> FEATURE:
<223> OTHER INFORMATION: Description of Artificial Sequence: Synthetic
      N. sylvestris peroxidase gene

<400> SEQUENCE: 3
atgagcttcc tccgcttcgt gggcgccatc ctgttcctgg tggccatctt cggcgccagc    60
aacgcccagc tgagcgccac cttctacgac accacctgcc ccaacgtgac cagcatcgtg   120
cgcggcgtga tggaccagcg ccagcgcacc gacgcccgcg ccggcgccaa gatcatccgc   180
ctgcacttcc acgactgctt cgtgaacggc tgcgacggca gcatcctgct ggacaccgac   240
ggcacccaga ccgagaagga cgctcctgcc aacgtgggcg ccggcggctt cgacatcgtg   300
gacgacatca agaccgccct cgagaacgtg tgccccggag tggtgagctg cgccgacatc   360
ctggccctcg cgagcgagat cggcgtggtg ctggccaagg ccctagctg  caggtgctg    420 ttcggccgca aggacagcct gactgccaac gcagcggcg  ccaacagcga catccccagc   480
cccttcgaga ccctggccgt gatgatcccc cagttcacca caagggcat  ggacctgacc   540 gacctggtgg ccctgagcgg cgcccacacc ttcggtcgag cccgctgcgg caccttcgag   600
cagagactgt tcaacttcaa cggcagcggc aaccccgacc tgaccgtgga cgccaccttc   660
ctgcagaccc tccagggcat ctgccccag  ggcggcaaca acggcaacac cttcaccaac   720
ctggacatca gcacccccaa cgacttcgac aacgactact tcaccaacct ccagagcaac   780
cagggcctgc tccagaccga ccaggagctg ttcagcacca gcggcagcgc caccatcgcc   840
atcgtgaacc gctacgccgg cagccagacc cagttcttcg acgacttcgt gagcagcatg   900
atcaagctgg gcaacatcag tcccctgacc ggcaccaacg gccagatccg caccgactgc   960
aagcgcgtga actag                                                    975
```

```
<210> SEQ ID NO 4
<211> LENGTH: 975
<212> TYPE: DNA
<213> ORGANISM: Artificial Sequence
<220> FEATURE:
<223> OTHER INFORMATION: Description of Artificial Sequence: Synthetic
      N. tomentisiformis peroxidase gene

<400> SEQUENCE: 4
atgagcttcc tgcgcttcgt gggcaccatc ctgttcctcg ttgccatctt cgccgccagc      60
aacgcccagc tgagcgccac cttctacgac agcacctgcc ccaacgtgac cagcatcgtg     120
cgcggcgtga tggaccagcg ccagcgcacc gacgcccgcg ccggcgccaa gatcatccgc     180
ctgcacttcc acgactgctt cgtgaacggc tgcgacggca gcatcctgct ggacaccgac     240
ggcacccaga ccgagaagga cgctgctccc aacgtgggcg ccggcggctt cgacatcgtg     300
gacgacatca agaccgccct cgagaacgtg tgccccggag tggtgagctg cgccgacatc     360
ctgagcctcg cgagcgagat cggcgtggcg ctggccgagg gccctagctg gcaggtgctg     420
ttcggccgca agaacagcct gactgccaac cgcagcgagg ccaacagcga catccccagc     480
cccttcgaga ccccgccgt gatgaccccc ctgttcacca acaagggcat ggacctgacc     540
gacctggtgg cccagagcgg cgcccacacc ttcggtcgag cccgctgcgg caccttcgag     600
cagagactgt tcaacttcag cggcagcggc aaccccgacc ccaccgtgga cgccaccttc     660
ctccagaccc tgcagggcat ctgccccag ggcggcaaca acggcaacac cttcaccaac     720
ctggacatca gcacccccaa cgacttcgac aacgactact tcaccaacct ccagaacaac     780
caaggcctgc tccagaccga ccaggagctg ttcagcacca gcggcagcgc caccatcgcc     840
atcgtgaacc gctacgccgg cagccagacc cagttcttcg acgacttcgt gagcagcatg     900
atcaagctgg gcaacatcag tccctgacc ggcaccaacg gcgagatccg caccgactgc     960
aagcgcgtga actag                                                      975

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: PCR primer
      N-TERM2B

<400> SEQUENCE: 5
gaagatctaa gttgacaatc atgtctttt                                        28

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: PCR primer
      C-TERM2B

<400> SEQUENCE: 6
gaagatctaa ttaaccctct tgcaatctc                                        29
```

PEROXIDASE GENE SEQUENCES

FIELD OF THE INVENTION

The present invention generally relates to novel peroxidase gene sequences and more particularly to synthetic peroxidase gene sequences optimized for expression in plants. The present invention also relateds methods of making and methods of using the novel peroxidase gene sequences to control insects.

BACKGROUND OF THE INVENTION

Insect pests are a major factor in the loss of the world's commercially important agricultural crops. Broad spectrum chemical pesticides have been used extensively to control or eradicate pests of agricultural importance. Although insecticides have been effective in controlling most harmful insects, there are considerable problems associated with the use of these compounds. Insecticides are expensive and costly to apply. Often repeated applications are necessary for effective control. There is also concern that insects have or will become resistant to many of the chemicals used in controlling them. Insecticides often kill beneficial insects which are pollinators or prey on the herbivorous insects. Additionally, there are environmental hazards associated with the long term use of chemical insecticides.

Programs of pest management are being introduced which lower the use of chemical insecticides. These programs include the improvement of crops by selection, the employment of biological control agents and insect predators, and the incorporation of insect resistant genes through breeding programs and genetic engineering. The most widely utilized genes for genetic engineering are the crystal protein genes from *Bacillus thuringiensis*. See, for example, Rice et al., EP-A-292 435 and Koziel et al., WO 93/07278. The majority of the crystal proteins made by Bacillus are toxic to larvae of insects in the orders Lepidoptera, Diptera and Coleoptera. In general, when an insecticidal crystal protein is ingested by a susceptible insect, the crystal is solubilized and acts as a toxic moiety. To avoid the development of insects which are resistant to these toxins, additional toxins are needed which have additive or synergistic affects.

Peroxidases are a subclass of oxido-reductases that use a peroxide such as $H_2O_2$ as substrate. Peroxidases are heme-containing monomeric glycoproteins able to bind divalent cations (mainly $Ca^{2+}$, but also $Mn^{2+}$) (Maranon and Van Huystee, *Phytochemistry* 37: 1217–1225 (1994)). The prosthetic groups for peroxidase have different roles. While the heme group is involved in catalysis, the divalent cations stabilize the heme moiety, and the glycosyl groups may help to stabilize the peroxidase by decreasing its turnover rate (Maranon and Van Huystee, *Phytochemistry* 37: 1217–1225 (1994)).

Peroxidases are often grouped into anionic, cationic, and neutral forms according to their migration on isoelectric focusing gels. Although as enzymes they are considered to have wide substrate specificity, they do appear to have some substrate "preferences" for different isoenzymes (Van Huystee, *Ann. Rev. Plant Physiol.*, 205–219 (1987)). There are several types of peroxidases and related enzymes including guaiacol peroxidase, NADH peroxidase, cytochrome-C peroxidase, catalase, glutathione peroxidase, L-ascorbate peroxidase, and manganese peroxidase.

In plants, peroxidases are monomeric proteins which are highly complex enzymes whose activities are closely regulated by the plant. Peroxidases are critical in the biosynthesis of plant cell walls. Peroxidases promote the peroxidative A tobacco anionic peroxidase has been utilized to transform *N. tabacum* and *N. sylvestris* (Lagrimini, *Plant Cell* 2:7–18 (1990); Lagrimini, *Plant Physiology* 96:577–583 (1991); both of which are incorporated herein by reference). These transgenic plants constitutively overexpressed a tobacco anionic peroxidase from a CaMV 35S promoter. The same construct has also been utilized to transform tomato plants (Lagrimini et al., *J. Am. Soc. Hort. Sci.* 117:1012–1016 (1992); Lagrimini et al., *Hortscience* 28:218–221(1993); both of which are incorporated herein by reference). Some tissues of these transgenic dicotyledonous plants expressing a tobacco anionic peroxidase gene were resistant to some insects (Dowd et al., presentation at the National Meeting of the Entomological Society of America, Indianapolis, December 1993).

In addition, the tobacco anionic peroxidase has been utilized to transform *Zea maize* (WO 98/27218). These transgenic plants constitutively overexpressed a tobacco anionic peroxidase from a CaMV 35S promoter. Maize leaves expressing the tobacco anionic peroxidase enzyme conferred 100% mortality against *Ostrinia nubilalis* (European corn borer) and *Heliothis zea* (Corn earworm), and also had a strong antifeeding effect against *Spodoptera frugiperda* (Fall armyworm).

Despite the previous successes realized by incorporation of insect resistant genes through breeding programs and genetic engineering, there remains a long-felt but unfulfilled need to discover new and effective insect control agents. Particularly needed are control agents that are targeted to economically important insect pests and that efficiently control insect strains resistant to existing insect control agents. Furthermore, agents whose application minimizes the burden on the environment are desirable.

SUMMARY OF THE INVENTION

The present invention addresses the aforementioned needs by providing novel peroxidase gene sequences, including synthetic peroxidase gene sequences optimized for expression in plants. The peroxidase enzymes encoded by the novel gene sequences are highly active against economically important insect pests such as *Ostrinia nubilalis* (European corn borer), *Heliothis zea* (Corn earworm), and *Spodoptera frugiperda* (Fall armyworm). The peroxidase enzymes can be used in multiple insect control strategies, resulting in maximal efficiency with minimal impact on the environment.

Hence, in one embodiment, the present invention is directed to an isolated nucleic acid molecule comprising a nucleotide sequence that encodes a *Nicotiana tomentisiformis* anionic peroxidase. In another embodiment, the present invention is directed to an isolated nucleic acid molecule comprising a nucleotide sequence that encodes an anionic peroxidase that comprises the amino acid sequence set forth in SEQ ID NO:2. In a particularly preferred embodiment, the present invention is directed to an isolated nucleic acid molecule comprising a nucleotide sequence that encodes an anionic peroxidase, wherein the nucleotide sequence is SEQ ID NO:1.

The present invention is further directed to a nucleic acid molecule comprising a synthetic nucleotide sequence that encodes an anionic peroxidase, wherein the synthetic nucleotide sequence has been optimized for expression in plants. In a preferred embodiment, the synthetic nucleotide sequence is SEQ ID NO:3 or SEQ ID NO:4.

The present invention is further directed to an isolated nucleic acid molecule comprising a nucleotide sequence that encodes an anionic peroxidase, wherein said nucleotide sequence comprises a 20, 25, 30, 35, 40, 45, or 50 (preferably 20) base pair nucleotide portion identical in sequence to a respective consecutive 20, 25, 30, 35, 40, 45, or 50 (preferably 20) base pair nucleotide portion of SEQ ID NO:3 or SEQ ID NO:4.

The present invention also provides a chimeric gene comprising a heterologous promoter sequence operatively linked to a nucleic acid molecule of the invention. Further, the present invention provides a recombinant vector comprising such a chimeric gene. Still further, the present invention provides a host cell comprising such a chimeric gene. A host cell according to this aspect of the invention may be a bacterial cell, a yeast cell, or a plant cell, preferably a plant cell. Even further, the present invention provides a plant comprising such a plant cell. Preferably, the plant is one of the following agronomically important crops: maize, rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, squash, pumpkin, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum, and sugarcane. Most preferably, the plant is maize.

In yet another aspect, the present invention provides an anionic peroxidase produced by the expression of DNA molecules of the present invention. According to a preferred embodiment, the peroxidase of the invention has activity against *Ostrinia nubilalis* (European corn borer), *Heliothis zea* (Corn earworm), and *Spodoptera frugiperda* (Fall armyworm). According to an especially preferred embodiment, a peroxidase of the invention comprises the amino acid sequence set forth in SEQ ID NO:2.

In a further aspect, the present invention provides a method of producing an insect-resistant plant, comprising introducing a nucleic acid molecule of the invention into the plant, wherein the nucleic acid molecule is expressible in the plant in an effective amount to control insects. According to a preferred embodiment, the insects are *Ostrinia nubilalis* (European corn borer), *Heliothis zea* (Corn earworm), and *Spodoptera frugiperda* (Fall armyworm).

In a still further aspect, the present invention provides a method of controlling insects comprising delivering to the insects an effective amount of a peroxidase according to the present invention. According to a preferred embodiment, the insects are Ostrinia nubilalis (European corn borer), *Heliothis zea* (Corn earworm), and *Spodoptera frugiperda* (Fall armyworm). Preferably, the peroxidase is delivered to the insects orally.

Other aspects and advantages of the present invention will become apparent to those skilled in the art from a study of the following description of the invention and non-limiting examples.

DEFINITIONS

"Activity" of the peroxidases of the invention is meant that the peroxidases function as orally active insect control agents, have a peroxidases effect, or are able to disrupt or deter insect feeding, which may or may not cause death of the insect. When a peroxidase of the invention is delivered to the insect, the result is typically death of the insect, or the insect does not feed upon the source that makes the peroxidase available to the insect.

"Associated with/operatively linked" refer to two nucleic acid sequences that are related physically or functionally. For example, a promoter or regulatory DNA sequence is said to be "associated with" a DNA sequence that codes for an RNA or a protein if the two sequences are operatively linked, or situated such that the regulator DNA sequence will affect the expression level of the coding or structural DNA sequence.

A "chimeric gene" is a recombinant nucleic acid sequence in which a promoter or regulatory nucleic acid sequence is operatively linked to, or associated with, a nucleic acid sequence that codes for an mRNA or which is expressed as a protein, such that the regulator nucleic acid sequence is able to regulate transcription or expression of the associated nucleic acid sequence. The regulator nucleic acid sequence of the chimeric gene is not normally operatively linked to the associated nucleic acid sequence as found in nature.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

To "deliver" a peroxidase means that the peroxidase comes in contact with an insect, resulting in toxic effect and control of the insect. The peroxidase can be delivered in many recognized ways, e.g., orally by ingestion by the insect or by contact with the insect via transgenic plant expression, formulated protein composition(s), sprayable protein composition(s), a bait matrix, or any other art-recognized toxin delivery system.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter which initiates transcription only when the host cell is exposed to some particular external stimulus. In the case of a multicellular organism, such as a plant, the promoter can also be specific to a particular tissue, or organ, or stage of development.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. A gene may also comprise other 5' and 3' untranslated sequences and termination sequences. Further elements that may be present are, for example, introns.

"Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "heterologous" nucleic acid sequence is a nucleic acid sequence not naturally associated with a host cell into which it is introduced, including non-naturally occurring multiple copies of a naturally occurring nucleic acid sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Insecticidal" is defined as a toxic biological activity capable of controlling insects, preferably by killing them.

A nucleic acid sequence is "isocoding with" a reference nucleic acid sequence when the nucleic acid sequence encodes a polypeptide having the same amino acid sequence as the polypeptide encoded by the reference nucleic acid sequence.

An "isolated" nucleic acid molecule or an isolated enzyme is a nucleic acid molecule or enzyme that, by the hand of man, exists apart from its native environment and is therefore not a product of nature. An isolated nucleic acid molecule or enzyme may exist in a purified form or may exist in a non-native environment such as, for example, a recombinant host cell.

A "nucleic acid molecule" or "nucleic acid sequence" is a linear segment of single- or double-stranded DNA or RNA that can be isolated from any source. In the context of the present invention, the nucleic acid molecule is preferably a segment of DNA. "ORF" means open reading frame.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo. "Plant tissue" as used herein means a group of plant cells organized into a structural and functional unit.

Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "promoter" is an untranslated DNA sequence upstream of the coding region that contains the binding site for RNA polymerase 11 and initiates transcription of the DNA. The promoter region may also include other elements that act as regulators of gene expression.

A "protoplast" is an isolated plant cell without a cell wall or with only parts of the cell wall.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.

"Synthetic" refers to a nucleotide sequence comprising structural characters that are not present in the natural sequence. For example, an artificial sequence that resembles more closely the G+C content and the normal codon distribution of dicot and/or monocot genes is said to be synthetic.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed" "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (lie; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V). Furthermore, (Xaa; X) represents any amino acid.

BRIEF DESCRIPTION OF THE SEQUENCES IN THE SEQUENCE LISTING

SEQ ID NO:1 is the nucleotide sequence of a native *Nicotiana tomentisiformis* anionic peroxidase gene.
SEQ ID NO:2 is the amino acid sequence of the anionic peroxidase encoded by SEQ ID NO:1.
SEQ ID NO:3 is the nucleotide sequence of a synthetic *Nicotiana sylvestris* anionic peroxidase gene optimized for expression in plants.
SEQ ID NO:4 is the nucleotide sequence of a synthetic *Nicotiana tomentisiformis* anionic peroxidase gene optimized for expression in plants.
SEQ ID NO:5 is PCR primer N-TERM2B used in Example 1.
SEQ ID NO:6 is PCR primer C-TERM2B used in Example 1.

DETAILED DESCRIPTION OF THE INVENTION

This invention relates to novel peroxidase gene sequences, including synthetic peroxidase gene sequences optimized for expression in plants. The peroxidase enzymes encoded by the novel gene sequences are highly active against economically important insect pests such as *Ostrinia nubilalis* (European corn borer), *Heliothis zea* (Corn earworm), and *Spodoptera frugiperda* (Fall armyworm). The peroxidase enzymes can be used in multiple insect control strategies, resulting in maximal efficiency with minimal impact on the environment.

According to one embodiment, the present invention is directed to a nucleic acid molecule comprising a nucleotide sequence isolated from *Nicotiana tomentisiformis* that encodes an anionic peroxidase. A native *Nicotiana tomentisiformis* anionic peroxidase gene sequence is set forth in SEQ ID NO:1 and the encoded amino acid sequence is set forth in SEQ ID NO:2.

According to another embodiment, the present invention is directed to a nucleic acid molecule comprising a synthetic nucleotide sequence that encodes an anionic peroxidase, wherein the synthetic nucleotide sequence has been optimized for expression in plants. Although in many cases heterologous genes can be expressed in plants at high levels without modification, low expression in transgenic plants may result from nucleotide sequences having codons that are not preferred in the transgenic plants. It is known in the art that all organisms have specific preferences for codon usage, and the codons of the nucleotide sequences described in this invention can be changed to conform with particular plant preferences, while maintaining the amino acids encoded thereby. Furthermore, high expression in plants is best achieved from coding sequences that have at least 35% about GC content, preferably more than about 45%, more preferably more than about 50%, and most preferably more than about 60%. Nucleotide sequences which have low GC contents may express poorly in plants due to the existence of ATTTA motifs which may destabilize messages, and AATAAA motifs which may cause inappropriate polyadenylation. Although preferred gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17: 477–498 (1989)). In addition, the nucleotide sequences are screened for the existence of illegitimate splice sites that may cause message truncation. Changes required to be made within the nucleotide sequences such as those described above are made using techniques of site directed mutagenesis, PCR, and synthetic gene construction and the methods described in the published patent applications EP 0 385 962 (to Monsanto), EP 0 359 472 (to Lubrizol, and WO 93/07278 (to Ciba-Geigy), each of which is incorporated herein by reference.

In a preferred embodiment, the methodology described in WO 93/07278 is used to create the synthetic nucleotide sequences shown in SEQ ID NO:3 and SEQ ID NO:4. The synthetic nucleotide sequence shown in SEQ ID NO:3 encodes the same amino acid sequence as that encoded by the *Nicotiana sylvestris* anionic peroxidase gene disclosed in genbank accession J02979. Hence, SEQ ID NO:3 is referred to as a synthetic *Nicotiana sylvestris* anionic peroxidase gene. The synthetic nucleotide sequence shown in SEQ ID NO:4 encodes the same amino acid sequence as that encoded by SEQ ID NO:1, i.e., SEQ ID NO:2. Hence, SEQ ID NO:4 is referred to as a synthetic *Nicotiana tomentisiformis* anionic peroxidase gene.

The present invention also encompasses recombinant vectors comprising the nucleic acid sequences of this invention. In such vectors, the nucleic acid sequences are preferably comprised in expression cassettes comprising regulatory elements for expression of the nucleotide sequences in a host cell capable of expressing the nucleotide sequences. Such regulatory elements usually comprise promoter and termination signals and preferably also comprise elements allowing efficient translation of polypeptides encoded by the nucleic acid sequences of the present invention. Vectors comprising the nucleic acid sequences are usually capable of replication in particular host cells, preferably as extrachromosomal molecules, and are therefore used to amplify the nucleic acid sequences of this invention in the host cells. In a preferred embodiment, host cells for such vectors are plant cells. In another preferred embodiment, such vectors are viral vectors and are used for replication of the nucleotide sequences in particular host cells, e.g. plant cells. Recombinant vectors are also used for transformation of the nucleotide sequences of this invention into host cells, whereby the nucleotide sequences are stably integrated into the DNA of such host cells. In a preferred embodiment, the host cells are plant cells, such as maize cells.

In a particularly preferred embodiment, the peroxidase of the invention is expressed in a plant. In this case, transgenic plants expressing effective amounts of the peroxidase protect themselves from insect pests. When the insect starts feeding on such a transgenic plant, it also ingests the expressed peroxidase. This will deter the insect from further biting into the plant tissue or may even harm or kill the insect. A nucleotide sequence of the present invention is inserted into an expression cassette, which is then preferably stably integrated in the genome of said plant. In another preferred embodiment, the nucleotide sequence is included in a non-pathogenic self-replicating virus. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa. rice, potato, eggplant, cucumber, Arabidopsis, and woody plants such as coniferous and deciduous trees. Preferably, the transgenic plants of the invention are monocots such as maize, rice, wheat, barley, oats, and sorghum.

For efficient initiation of translation, sequences adjacent to the initiating methionine may require modification. For example, they can be modified by the inclusion of sequences known to be effective in plants. Joshi has suggested an appropriate consensus for plants (NAR 15: 6643–6653 (1987)) and Clontech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (whilst leaving the second amino acid unmodified), or alternatively up to and including the GTC subsequent to the ATG (with the possibility of modifying the second amino acid of the transgene).

Expression of the nucleotide sequences in transgenic plants is driven by promoters shown to be functional in plants. The choice of promoter will vary depending on the temporal and spatial requirements for expression, and also depending on the target species. Thus, expression of the nucleotide sequences of this invention in leaves, in ears, in inflorescences (e.g. spikes, panicles, cobs, etc.), in roots, and/or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Preferred promoters that are expressed constitutively include promoters from genes encoding actin or ubiquitin and the CaMV 35S and 19S promoters. The nucleotide sequences of this invention can also be expressed under the regulation of promoters that are chemically regulated. This enables the peroxidases to be synthesized only when the crop plants are treated with the inducing chemicals. Preferred technology for chemical induction of gene expression is detailed in the published application EP 0 332 104 (to Ciba-Geigy) and U.S. Pat. No. 5,614,395. A preferred promoter for chemical induction is the tobacco PR-1a promoter.

A preferred category of promoters is that which is wound inducible. Numerous promoters have been described which are expressed at wound sites and also at the sites of phytopathogen infection. Ideally, such a promoter should only be active locally at the sites of infection, and in this way the peroxidases only accumulate in cells which need to synthesize the peroxidases to kill the invading insect pest. Preferred promoters of this kind include those described by Stanford et al. Mol. Gen. Genet. 215: 200–208 (1989), Xu et al. Plant Molec. Biol. 22: 573–588 (1993), Logemann et al. *Plant Cell* 1: 151–158 (1989), Rohrmeier & Lehle, Plant Molec. Biol. 22: 783–792 (1993), Firek et al. Plant Molec. Biol. 22: 129–142 (1993), and Warner et al. Plant J. 3: 191–201 (1993).

Preferred tissue specific expression patterns include green tissue specific, root specific, stem specific, and flower specific. Promoters suitable for expression in green tissue include many which regulate genes involved in photosynthesis and many of these have been cloned from both monocotyledons and dicotyledons. A preferred promoter is the maize PEPC promoter from the phosphoenol carboxylase gene (Hudspeth & Grula, *Plant Molec. Biol.* 12: 579–589 (1989)). A preferred promoter for root specific expression is that described by de Framond (*FEBS* 290: 103–106 (1991); EP 0 452 269 to Ciba-Geigy). A preferred stem specific promoter is that described in U.S. Pat. No. 5,625,136 (to Ciba-Geigy) and which drives expression of the maize trpA gene.

Especially preferred embodiments of the invention are transgenic plants expressing at least one of the nucleotide sequences of the invention in a root-preferred or root-specific fashion. Further preferred embodiments are transgenic plants expressing the nucleotide sequences in a wound-inducible or pathogen infection-inducible manner.

In addition to the selection of a suitable promoter, constructions for expression of peroxidases in plants require an appropriate transcription terminator to be attached downstream of the heterologous nucleotide sequence. Several such terminators are available and known in the art (e.g. tm1 from CaMV, E9 from rbcS). Any available terminator known to function in plants can be used in the context of this invention.

Numerous other sequences can be incorporated into expression cassettes described in this invention. These include sequences which have been shown to enhance expression such as intron sequences (e.g. from Adh1 and bronze1) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Subcellular localization of transgene encoded enzymes is undertaken using techniques well known in the art. Typically, the DNA encoding the target peptide from a known organelle-targeted gene product is manipulated and fused upstream of the nucleotide sequence. Many such target sequences are known for the chloroplast and their functioning in heterologous constructions has been shown. The expression of the nucleotide sequences of the present invention is also targeted to the endoplasmic reticulum or to the vacuoles of the host cells. Techniques to achieve this are well-known in the art.

Vectors suitable for plant transformation are described elsewhere in this specification. For Agrobacterium-mediated transformation, binary vectors or vectors carrying at least one T-DNA border sequence are suitable, whereas for direct gene transfer any vector is suitable and linear DNA containing only the construction of interest may be preferred. In the case of direct gene transfer, transformation with a single DNA species or co-transformation can be used (Schocher et al. *Biotechnology* 4: 1093–1096 (1986)). For both direct gene transfer and Agrobacterium-mediated transfer, transformation is usually (but not necessarily) undertaken with a selectable marker which may provide resistance to an antibiotic (kanamycin, hygromycin or methotrexate) or a herbicide (basta). Examples of such markers are neomycin phosphotransferase, hygromycin phosphotransferase, dihydrofolate reductase, phosphinothricin acetyltransferase, 2, 2-dichloroproprionic acid dehalogenase, acetohydroxyacid synthase, 5-enolpyruvyl-shikimate-phosphate synthase, haloarylnitrilase, protoporhyrinogen oxidase, acetylcoenzyme A carboxylase, dihydropteroate synthase, chloramphenicol acetyl transferase, and β-glucuronidase. The choice of selectable or screenable marker for plant transformation is not, however, critical to the invention.

The recombinant DNA described above can be introduced into the plant cell in a number of art-recognized ways. Those skilled in the art will appreciate that the choice of method might depend on the type of plant targeted for transformation. Suitable methods of transforming plant cells include microinjection (Crossway et al., *Bio Techniques* 4:320–334 (1986)), electroporation (Riggs et al., *Proc. Natl. Acad. Sci. USA* 83:5602–5606 (1986), Agrobacterium-mediated transformation (Hinchee et al., Biotechnology 6:915–921 (1988); See also, Ishida et al., *Nature Biotechnology* 14745–750 (June 1996) for maize transformation), direct gene transfer (Paszkowski et al., *EMBO J.* 3:2717–2722 (1984); Hayashimoto et al., *Plant Physiol.* 93:857–863 (1990)(rice)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923–926 (1988)). See also, Weissinger et al., *Annual Rev. Genet.* 22:421–477 (1988); Sanford et al., *Particulate Science and Technology* 5:27–37 91987)(onion); Svab et al., *Proc. Natl. Acad. Sci. USA* 87: 8526–8530 (1990) (tobacco chloroplast); Christou et al., *Plant Physiol.* 87:671–674 (1988)(soybean); McCabe et al., Bio/Technology 6:923–926 (1988)(soybean); Klein et al., *Proc. Natl. Acad. Sci. USA*, 85:4305–4309 (1988)(maize); Klein et al., Bio/Technology 6:559–563 (1988) (maize); Klein et al., *Plant Physiol.* 91:440–444 (1988) (maize); Fromm et al., *Bio/Technology* 8:833–839 (1990); and Gordon-Kamm et al., *Plant Cell* 2:603–618 (1990) (maize); Koziel et al., Biotechnology 11: 194–200 (1993) (maize); Shimamoto et al., *Nature* 338:274–277 (1989) (rice); Christou et al., *Biotechnolgy* 9: 957–962 (1991) (rice); Datta et al., *Bio/Technology* 8:736–740 (1990) (rice); European Patent Application EP 0 332 581 (orchardgrass and other Pooideae); Vasil et al., *Biotechnolgy* 11: 1553–1558 (1993) (wheat); Weeks et al., *Plant Physiol.* 102:1077–1084 (1993) (wheat); Wan et al., *Plant Physiol.* 104: 37–48 (1994) (barley); Jahne et al., *Theor. Appl. Genet.* 89:525–533 (1994)(barley); Umbeck et al., Bio/Technology 5: 263–266 (1987) (cotton); Casas et al., *Proc. Natl. Acad. Sci. USA* 90:11212–11216 (December 1993) (sorghum); Somers et al., Bio/Technology 10:1589–1594 (December 1992) (oat); Torbert et al., *Plant Cell Reports* 14:635–640 (1995) (oat); Weeks et al., *Plant Physiol.* 102:1077–1084 (1993) (wheat); Chang et al., WO 94/13822 (wheat) and Nehra et al., *The Plant Journal* 5:285–297 (1994) (wheat). A particularly preferred set of embodiments for the introduction of recombinant DNA molecules into maize by microprojectile bombardment can be found in Koziel et al., *Biotechnolgy* 11: 194–200 (1993), Hill et al., *Euphytica* 85:119–123 (1995) and Koziel et al., Annals of the New York Academy of *Sciences* 792:164–171 (1996). An additional preferred embodiment is the protoplast transformation method for maize as disclosed in EP 0 292 435. Transformation of plants can be undertaken with a single DNA species or multiple DNA species (i.e. co-transformation) and both these techniques are suitable for use with the peroxidase coding sequence.

In another preferred embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al. (1994) *Proc. Nati. Acad. Sci. USA* 91, 7301–7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P. (1990) *Proc. Natl. Acad. Sci. USA* 87, 8526–8530; Staub, J. M., and Maliga, P. (1992) *Plant Cell* 4, 39–45). This resulted in stable homoplasmic transformants at a frequency of approximately one per 100 bombardments of target leaves. The presence of cloning sites between these markers allowed creation of a plastid targeting vector for introduction of foreign genes (Staub, J. M., and Maliga, P. (1993) *EMBO J.* 12, 601–606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P. (1993) *Proc. Natl. Acad. Sci. USA* 90, 913–917). Previously, this marker had been used successfully for high-frequency transformation of the plastid genome of the green alga *Chlamydomonas reinhardtii* (Goldschmidt-Clermont, M. (1991) *Nucl. Acids Res.* 19: 4083–4089). Other selectable markers useful for plastid transformation are known in the art and encompassed within the scope of the invention. Typically, approximately 15–20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

The peroxidase coding sequence may be used alone or in combination. That is, one or more peroxidase coding sequences can be inserted into a plant to control different insect pests. This can be accomplished by (1) transforming a host plant with a DNA sequence comprising more than one peroxidase coding sequence, (2) transforming a host plant with a DNA sequence comprising a single peroxidase coding sequence and identifying multiple insertions of the DNA sequence into the host genome, or (3) repeated transformation of a host plant with a peroxidase coding sequence until the host plant comprises the desired number of peroxidase coding sequences.

The level of insect protection of a plant against a given insect and/or its spectrum of insecticidal activities can also be increased by combining a peroxidase coding sequence with other coding sequences encoding proteins capable of controlling insects.

*Bacillus thuringiensis* (Bt) is a gram-positive, spore-forming bacterium which produces a parasporal crystal during sporulation (For review see, Koziel et al., *Biotech. and Gen. Engin. Reviews* 11:171–228 (1993)). These crystals are predominantly comprised of one or more porteins, called δ-endotoxins or insecticidal crystal proteins, known to possess insecticidal activity when ingested by certain insects. Numerous strains of Bt are currently known. Each strain produces differing numbers of δ-endotoxins with various insecticidal activities. Examples of Bt endotoxins which can be used in combination with peroxidases include, but are not restricted to CryIA(b) (Koziel et al., *Bio/Technology* 11: 194–200 (1993)), CryIA(c) (U.S. Pat. No. 5,530, 197), Cry1H (also called Cry9C) (Lambert et al. *Appl. Environ. Microbiol.* 62:80–86 (1996)), and CryIIIA (Adang et al. *Plant Mol. Biol.* 21:1131–1145 (1993).

Pesticidal proteins produced during vegetative growth of Bacillus strains (vegetative insecticidal proteins, VIPs) can also be used in combination with peroxidases. For examples of VIPs see, Warren et al., WO 94/21795; Warren et al., WO 96/10083; Estruch et al., U.S. Pat. No. 5,877,012; and Estruch et al., *Proc. Natl. Acad. Sci. USA* 93: 5389–5394 (1996).

Examples of other proteins with insecticidal compounds which can be used in combination with peroxidases include, but are not restricted to, cholesterol oxidases (U.S. Pat. No. 5,518,908), protease inhibitors, lectins, and α-amylases.

Plants expressing more than one insect resistance coding sequence can be made by any method known in the art. For example, the peroxidase coding sequence can be used to transform a plant at the same time as another insect principle gene (cotransformation), the second insect principle gene can be introduced into a plant which has already been transformed with a peroxidase coding sequence, or by vice versa, or alternatively, transgenic plants, one expressing a peroxidase coding sequence and one expressing a second insect principle can be crossed to bring the coding sequences together in the same plant.

Once a chimeric gene comprising a peroxidase coding sequence of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the peroxidase coding sequence in the transgenic plant is sexually transmitted. In one preferred embodiment, the peroxidase coding sequence is sexually transmitted through a complete normal sexual cycle of the R0 plant to the R1 generation. Additionally preferred, the peroxidase coding sequence is expressed so that the level of peroxidase in the cells, tissues, seeds or plant is increased above the level in the cells, tissues, seeds or plant of a plant which only differ in that the peroxidase coding sequence is absent.

The invention further relates to a commercial bag comprising seed of a plant transformed with recombinant DNA comprising a coding sequence encoding peroxidase, wherein expression of peroxidase confers on said plant a phenotypic trait. Preferred within this invention is a commercial bag comprising seed of a transgenic plant wherein expression of peroxidase confers on said plant insect resistance or standability. A further preferred object of the invention is such a commercial bag together with lable instructions for the use of the seed contained therein.

The transgenic plants of the invention can be used in methods for controlling insects such as Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, and Trichoptera. Particular examples of such insect pests are European corn borer, stalk corn borer, black cutworm, corn earworm, fall armyworm, southwestern corn borer, lesser cornstalk borer, sugarcane borer, western corn rootworm, northern corn rootworm, southern corn rootworm, wireworms, northern masked chafer, southern masked chafer, Japanese beetle, corn flea beetle, maize billbug, corn leaf aphid, corn root aphid, chinch bug, redlegged grasshopper, migratory grasshopper, seedcorn maggot, corn blotch leafminer, grass thrips, thief ant and two-spotted spider mite.

In one preferred embodiment, the present invention relates to a method for controlling insects by feeding or contacting an insect with an insecticidal amount of transgenic plant cells, preferably monocotyledonous plant cells, wherein the genome of said plant cells encodes a peroxidase of the invention. Upon expression, the peroxidase confers insect resistance to the transgenic plant cells. The transgene encoding the peroxidase constitutes an additional gene inserted into the genome of a progenitor plant which does not naturally encode said peroxidase. Insect resistant plants comprise increased insect resistance over that found in native non-manipulated plants due to increased levels of peroxidase.

Maize plants of the present invention are preferably resistant to an insect or insects selected from the group which includes but is not limited to *Ostrinia nubilalis*, European corn borer; *Sesemia nonegrioides*, stalk corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer, *Diabrotica virgifera virgifera*, western corn rootworm, *Diabrotica longicornis barberi*, northern corn rootworm, *Diabrotica undecimpunctata howardi*, southern corn rootworm, Melanotus spp., wireworms, *Cyclocephala borealis*, northern masked chafer (white grub), *Cyclocephala immaculata*, southern masked chafer (white grub), *Popillia japonica*, Japanese beetle (grub and adult forms), *Chaetocnema pulicaria*, corn flea beetle, *Sphenophorus*

*maidis*, maize billbug, *Rhopalosiphum maidis*, corn leaf aphid, *Anuraphis maidiradicis*, corn root aphid, *Blissus leucopterus leucopterus*, chinch bug, *Melanoplus femurrubrum*, redlegged grasshopper, *Melanoplus sanguinipes*, migratory grasshopper, *Hylemya platura*, seedcorn maggot, *Agromyza parvicornis*, corn blotch leafminer, *Anaphothrips obscurus*, grass thrips, *Solenopsis milesta*, thief ant, and *Tetranychus urticae*, two-spotted spider mite.

Sorghum plants of the present invention are preferably resistant to an insect or insects selected from the group which includes but is not limited to *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranean*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis, maize billbug; Rhopalosiphum maidis*, corn leaf aphid; *Sipha flara*, yellow sugarcane aphid; *Blissus leucopterus leucopterus*, chinch bug; *Contarinia sorghicola*, sorghum midge; *Tetranychus cinnabarinus*, carmine spider mite; and *Tetranychus urticae*, twospotted spider mite.

Wheat plants of the present invention are preferably resistant to an insect or insects selected from the group which includes but is not limited to *Pseudaletia unipunctata*, army worm; *Spodoptera frugiperda*, fall armyworm; *Elasmopalpus lignosellus*, lesser cornstalk borer; *Agrotis orthogonia*, pale western cutworm; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; and *Aceria tulipae*, wheat curl mite.

Rice plants of the present invention are preferably resistant to an insect or insects selected from the group which includes but is not limited to *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; and *Acrosternum hilare*, green stink bug.

Barley plants of the present invention are preferably resistant to an insect or insects selected from the group which includes but is not limited to *Ostrinia nubilalis*, European corn borer; *Agrotis ipsilon*, black cutworm; *Schizaphis graminum*, greenbug; *Blissus leucopterus* leucopterus, chinch bug; *Acrosternum hilare*, green stink bug; *Euschistus servos*, brown stink bug; *Hylemya platura*, seedcorn maggot; *Mayetiola destructor*, Hessian fly; Thysanoptera, Thrips; and *Petrobia latens*, brown wheat mite.

Use of the advantageous genetic properties of the transgenic plants and seeds according to the invention can further be made in plant breeding which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pestidice treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD®), methalaxyl (Apron®), and pirimiphos-methyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989); and by T. J. Silhavy, M. L. Berman, and L. W. Enquist, Experiments with Gene Fusions, Cold Spring Harbor Laboratory, Cold Spring Harbor, N.Y. (1984).

A. Novel Peroxidase Coding Sequences

Example 1
Isolation of an Anionic Peroxidase cDNA from *Nicotiana tomentisiformis*

Total RNA is isolated from 4 week old leaves of *N. tomentisiformis* plants. Poly A+RNA is then obtained from total RNA using an oligo-dT affinity column. PCR primers (N-TERM2B: gaagatctaagttgacaatcatgtcttt (SEQ ID NO:5) and C-TERM2B: gaagatctaattaaccctcttgcaatctc (SEQ ID NO:6)) are synthesized based on the 5' and 3' ends of the coding region of the *N. sylvestris* peroxidase sequence (Lagrimini, *Plant Cell* 2:7–18 (1990); Lagrimini, *Plant Physiology* 96:577–583 (1991)). These primers amplify an 850-bp fragment in a RT-PCR reaction using *N. tomentisiformis* polyA+RNA. This fragment is gel purified and ligated into a pBluescript vector. Clones are obtained and sequenced. SEQ ID NO:1 is the cDNA sequence of a *Nicotiana tomentisiformis* anionic peroxidase gene, and SEQ ID NO:2 is the amino acid sequence of the *Nicotiana tomentisiformis* anionic peroxidase encoded by SEQ ID NO:1.

Example 2
Construction of a Synthetic *Nicotiana sylvestris* Peroxidase Gene A maize optimized peroxidase gene is designed by downloading the sequence of the native peroxidase gene cloned from *Nicotiana sylvestris*, from genbank accession J02979. The deduced amino acid from this sequence is backtranslated using the "Backtranslation" program found in the University of Wisconsin GCG group of programs using a maize preference codon table (Murray et al., *Nucl Acids Res.* 17:477–498, 1989, incorporated herein by reference). Only the most frequently used maize codon is used for each amino acid, as described in WO 93/07278. The resultant sequence is referred to as a "pure" maize optimized sequence. This results in a change of GC content of the peroxidase gene from 37% to 67%. The "pure" maize optimized sequence is changed further at nucleotide 672 from G to C, at nucleotide 771 from G to C, and at nucleotide 792 from G to C to remove three Pst restriction sites. Further, the G at nucleotide 321 is changed to C to insert a unique XhoI restriction site. The sequence GGATCCACC (comprising a BamHI restriction site and translation initiation codon neighbor Kozak consensus sequence) is inserted at the 5' end and a termination codon as well as sequence for restriction site SacI is added at the 3' end of the sequence. The gene is designed to be cloned in three fragments. The first fragment, nucleotides 1–332, is flanked by BamHI and XhoI endonuclease restriction enzyme sites. Fragment two, nucleotides 319–666, is flanked by restriction sites for XhoI and PstI. The third fragment is flanked by PstI and SacI sites. Each fragment is comprised of five pairs of oligonucleotides ranging in size between 40–88 nucleotides, but mostly about 60–65 nucleotides in length. Changes are made to thirteen more nucleotides during the designing of the oligonucleotides to reduce stable secondary structure formation in the single stranded DNA fragments. The sequences are checked to see that the resulting synthetic gene encodes a peptide sequence identical to that of the native gene.

The synthetic gene is constructed in three fragments. Each fragment is constructed by hybridization of ten pairs of oligomers 60–75 nucleotides in length representing both strands of the gene. A 15 nucleotide overlap is designed between sequential oligonucleotide pairs for correct orientation and assembly. Oligonucleotides may be synthesized by Genosys Biotechnologies Inc., TX. Each pair of oligomers is hybridized and phosphorylated using the enzyme polynucleotide kinase from New England Biolabs, Inc., MA using conditions specified by the vendor. Five kinased fragment pairs are then hybridized and ligated into a high copy plasmid vector containing an ampicillin resistance gene and transformed into competent DH5α cells. The cells are plated onto ampicillin containing media and incubated overnight at 37° C. Colonies are screened for inserted DNA. The DNA is sequenced and clones containing the correct sequence are selected. The three fragments are then joined by restriction digestion, ligation and transformation using the unique restriction sites between the fragnments, viz., XhoI to join fragments 1 and 2 and PstI to join fragments 2 and 3. The sequence of the complete gene is verified and the gene is cloned into plant expression vector cassettes for production of transgenic plants.

The nucleotide sequence of a synthetic *Nicotiana sylvestris* peroxidase gene optimized for expression in plants is presented in SEQ ID NO:3.

Example 3
Construction of a Synthetic *Nicotiana tomentisiformis* Peroxidase Gene The DNA sequence obtained in Example 1 is used as a template for the synthesis of a maize optimized *Nicotiana tomentisiformis* gene. Alignment of the native *Nicotiana tomentisiformis* and *Nicotiana sylvestris* peroxidase genes shows that there is a difference of 18 amino acids between the two genes; four in fragment 1, 11 in fragment two, and 2 in fragment three. Changes in fragments 1 and 3 are made by PCR mutagenesis using primers containing the specific changes. Fragment 2 is designed as described above in Example 2. The overlapping restriction sites between the fragments are the same as in the *Nicotiana syvestris* gene, XhoI between fragments 1 and 2 and PstI between fragments 2 and 3. The complete gene is constructed as described above in Example 2.

The nucleotide sequence of a synthetic *Nicotiana tomentisiformis* peroxidase gene optimized for expression in plants is presented in SEQ ID NO:4.

B. Expression of the Nucleotide Sequences in Transcienic Plants

The nucleic acid sequences described in this application can be incorporated into plant cells using conventional recombinant DNA technology. Generally, this involves inserting a coding sequence of the invention into an expression system to which the coding sequence is heterologous (i.e., not normally present) using standard cloning procedures known in the art. The vector contains the necessary elements for the transcription and translation of the inserted protein-coding sequences. A large number of vector systems known in the art can be used, such as plasmids, bacteriophage viruses and other modified viruses. Suitable vectors include, but are not limited to, viral vectors such as lambda vector systems λgtI1, λgtI0 and Charon 4; plasmid vectors such as pBI121, pBR322, pACYC177, pACYC184, pAR series, pKK223–3, pUC8, pUC9, pUC18, pUC19, pLG339, pRK290, pKC37, pKC101, pCDNAII; and other similar systems. The components of the expression system may also be modified to increase expression. For example, truncated sequences, nucleotide substitutions or other modifications may be employed. The expression systems described herein can be used to transform virtually any crop plant cell under suitable conditions. Transformed cells can be regenerated into whole plants such that the nucleotide sequence of the invention confer insect resistance to the transgenic plants.

Example 4
Construction of Plant Expression Cassettes

Coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

1. Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter:

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and Arabidopsis—Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The Arabidopsis ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter:

Construction of the plasmid pCGN1761 is described in the published patent application EP 0 392 225 (Example 23), which is hereby incorporated by reference. pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglII sites 3' to the terminator for transfer to transformation vectors such as those described below. Furthermore, the double 35S promoter fragment can be removed by 5' excision with HindIII, SphI, SalI, XbaII, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter:

Several isoforms of actin are known to be expressed in most cell types and consequently the actin promoter is a good choice for a constitutive promoter. In particular, the promoter from the rice ActI gene has been cloned and characterized (McElroy et al. *Plant Cell* 2: 163–171 (1990)). A 1.3kb fragment of the promoter was found to contain all the regulatory elements required for expression in rice protoplasts. Furthermore, numerous expression vectors based on the ActI promoter have been constructed specifically for use in monocotyledons (McElroy et al. *Mol. Gen. Genet.* 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (*Mol. Gen. Genet.* 231: 150–160 (1991)) can be easily modified for gene expression and are particularly suitable for use in monocotyledonous hosts. For example, promoter-containing fragments is removed from the McElroy constructions and used to replace the double 35S promoter in pCGN1761 ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506–509 (1993)).

d. Inducible Expression, the PR-1 Promoter:

The double 35S promoter in pCGN1761ENX may be replaced with any other promoter of choice that will result in suitably high expression levels. By way of example, one of the chemically regulatable promoters described in U.S. Pat. No. 5,614,395 may replace the double 35S promoter. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1 761 ENX (Uknes et al., 1992). pCIB1 004 is cleaved with NcoI and the resultant 3' overhang of the linearized fragment is rendered blunt by treatment with T4 DNA polymerase. The fragment is then cleaved with HindIiI and the resultant PR-1 a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1 761 ENX derivative with the PR-1 a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter:

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) *Nat. Biotechnol* 16:177–180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

f. Inducible Expression, a Glucocorticoid-lnducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the insecticidal toxin.

g. Root Specific Expression:

Another pattern of gene expression is root expression. A suitable root promoter is described by de Framond (FEBS 290: 103–106 (1991)) and also in the published patent application EP 0 452 269, which is herein incorporated by reference. This promoter is transferred to a suitable vector such as pCGN1761 ENX for the insertion of a selected gene and subsequent transfer of the entire promoter-gene-terminator cassette to a transformation vector of interest.

h. Wound-inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression:

Patent Application WO 93/07278, which is herein incorporated by reference, describes the isolation of the maize trpA gene, which is preferentially expressed in pith cells. The gene sequence and promoter extending up to –1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

k. Pollen-Specific Expression:

WO 93/07278 describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1 761 where it can replace the 35S promoter and be used to drive the expression of a nucleic acid sequence of the invention in a pollen-specific manner.

2. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., Genes Develop. 1: 1183–1200 (1987)). In the same experimental system, the intron from the maize bronzel gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693–8711 (1987); Skuzeski et al. Plant Molec. Biol. 15: 65–79 (1990)).

4. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104–15109 (1988)). These signal sequences can be fused to heterologous gene products to effect the import of heterologous products into the chloroplast (van den Broeck, et al. Nature 313: 358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512–6516 (1985)).

In addition, sequences have been characterized which cause the targeting of gene products to other cell compartments. Amino terminal sequences are responsible for targeting to the ER, the apoplast, and extracellular secretion from aleurone cells (Koehler & Ho, Plant Cell 2: 769–783 (1990)). Additionally, amino terminal sequences in conjunction with carboxy terminal sequences are responsible for vacuolar targeting of gene products (Shinshi et al. Plant Molec. Biol. 14: 357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081–1091 (1982) and Wasmann et al. Mol. Gen. Genet. 205: 446–453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Example 5

Construction of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptll gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), and the EPSPS gene, which confers resistance to glyphosate (U.S. Pat. Nos. 4,940,935 and 5,188,642).

1. Vectors Suitable for Agrobacterium Transformation

Many vectors are available for transformation using *Agrobacterium tumefaciens*. These typically carry at least one T-DNA border sequence and include vectors such as pBIN19 (Bevan, Nucl. Acids Res. (1984)) and pXYZ. Below, the construction of two typical vectors suitable for Agrobacterium transformation is described.

a. pCIB200 and pCIB2001:

The binary vectors pcIB200 and pCIB2001 are used for the construction of recombinant vectors for use with Agrobacterium and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between E. coli and other hosts, and the OriT and OriV functions also from RK2. The pCIB2001 polylinker is suitable for the cloning of plant expression cassettes containing their own regulatory signals.

b. pCIB10 and Hygromycin Selection Derivatives thereof:

The binary vector pCIB10 contains a gene encoding kanamycin resistance for selection in plants and T-DNA right and left border sequences and incorporates sequences from the wide host-range plasmid pRK252 allowing it to replicate in both E. coli and Agrobacterium. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

2. Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the E. coli GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 bp SmaI fragment containing the bargene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in E. coli) and a polylinker with the unique sites SphI, PstI, HindIII, and BamHI. This vector is suitable for the cloning of plant expression cassettes containing their own regulatory signals.

b. pSOG19 and pSOG35:

pSOG35 is a transformation vector that utilizes the E. coli gene dihydrofolate reductase (DFR) as a selectable marker conferring resistance to methotrexate. PCR is used to amplify the 35S promoter (~800 bp), intron 6 from the maize Adhl gene (~550 bp) and 18 bp of the GUS untranslated leader sequence from pSOG10. A 250-bp fragment encoding the E. coli dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG1 9 and pSOG35 carry the pUC gene for ampicillin resistance and have HindIII, SphI, PstI and EcoRI sites available for the cloning of foreign substances.

3. Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Example 6

Transformation

Once a nucleic acid sequence of the invention has been cloned into an expression system, it is transformed into a plant cell. Methods for transformation and regeneration of plants are well known in the art. For example, Ti plasmid vectors have been utilized for the delivery of foreign DNA, as well as direct DNA uptake, liposomes, electroporation, micro-injection, and microprojectiles. In addition, bacteria from the genus Agrobacterium can be utilized to transform plant cells. Below are descriptions of representative techniques for transforming both dicotyledonous and monocotyledonous plants, as well as a representative plastid transformation technique.

1. Transformation of Dicotyledons

Transformation techniques for dicotyledons are well known in the art and include Agrobacterium-based techniques and techniques that do not require Agrobacterium.

Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnolgy 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using *E. coli* carrying the recombinant binary vector, a helper *E. coli* strain which carries a plasmid such as pRK201 3 and which is able to mobilize the recombinant binary vector to the target Agrobacterium strain. Alternatively, the recombinant binary vector can be transferred to Agrobacterium by DNA transformation (Hofgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

2. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnolgy 4: 1093–1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnolgy 8: 833–839 (1990)) have published techniques for transformation of A188-derived maize line using particle bombardment. Furthermore, WO 93/07278 and Koziel et al. (Biotechnolgy 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnolgy 8: 736–740 (1990)). Both types are also routinely transformable using particle bombardment (Christou et al. Biotechnolgy 9: 957–962 (1991)). Furthermore, WO 93/21335 describes techniques for the transformation of rice via electroporation.

Patent Application EP 0 332 581 describes techniques for the generation, transformation and regeneration of Pooideae protoplasts. These techniques allow the transformation of Dactylis and wheat. Furthermore, wheat transformation has been described by Vasil et al. (Biotechnolgy 10: 667–674 (1992)) using particle bombardment into cells of type C long-term regenerable callus, and also by Vasil et al. (Biotechnolgy 11:1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using Agrobacterium has also been described. See, WO 94/00977 and U.S. Pat. No. 5,591,616, both of which are incorporated herein by reference.

3. Transformation of Plastids

Seeds of Nicotiana tabacum c.v. 'Xanthi nc' are germinated seven per plate in a 1" circular array on T agar medium and bombarded 12–14 days after sowing with 1 om tungsten particles (M10, Biorad, Hercules, Calif.) coated with DNA from plasmids pPH143 and pPH145 essentially as described (Svab, Z. and Maliga, P. (1993) PNAS 90, 913–917). Bombarded seedlings are incubated on T medium for two days after which leaves are excised and placed abaxial side up in bright light (350–500 umol photons/m$^2$/s) on plates of RMOP medium (Svab, Z., Hajdukiewicz, P. and Maliga, P. (1990) PNAS 87, 8526–8530) containing 500 µg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., 1989). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) PNAS 91, 7301–7305) and transferred to the greenhouse.

C. Insect Bioassays

The following are examples of insect bioassays performed with preferred transgenic plants of the invention.

Example 7

Maize Bioassays

Transgenic maize plants demonstrated to contain the peroxidase coding sequence by Southern analysis or PCR are originally evaluated for insecticidal activity against *Ostrinia nubilalis* (ECB). This first group of bioassays is performed by applying 10 first instar ECB larvae to a leaf cutting that has been placed into a Gelman petri dish with a moistened filter pad to prevent the leaf cutting from drying out. The larvae are allowed to feed undisturbed for two days. A percent mortality reading is taken after two days.

Transgenic maize plants expressing the peroxidase enzyme are also assayed for other insecticidal activity by means of additional insect bioassays known in the art. The procedure is similar for any maize plant transformed with any insecticidal gene but is described here using as an example a peroxidase coding sequence. One to four 4 cm sections are cut from an extended leaf of a transformed maize plant. Each leaf piece is placed on a moistened filter disc in a 50×9 mm petri dish. Five neonate larvae of the target insect are placed on each leaf piece. Each plant is sampled multiple times for a total of 5–20 larvae per plant.

The petri dishes are incubated at 30° C. and leaf feeding damage and mortality data are scored at 24, 48, and 72 hours. Maize plants demonstrated to contain the peroxidase coding sequence are also evaluated for insecticidal activity against, for example: *Sesemia nonegrioides*, stalk corn borer; Agrotis ipsilon, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, sugarcane borer, *Diabrotica virgifera virgifera*, western corn rootworm, *Diabrotica longicornis* barberi, northern corn rootworm, *Diabrotica undecimpunctata howardi*, southern corn rootworm, Melanotus spp., wireworms, *Cyclocephala borealis*, northern masked chafer (white grub), *Cyclocephala immaculata*, southern masked chafer (white grub), *Popillia japonica*, Japanese beetle (grub and adult forms), *Chaetocnema pulicaria*, corn flea beetle, *Sphenophorus maidis*, maize billbug, *Rhopalosiphum maidis*, corn leaf aphid, *Anuraphis maidiradicis*, corn root aphid, *Blissus leucopterus leucopterus*, chinch bug, *Melanoplus femurrubrum*, redlegged grasshopper, *Melanoplus sanguinipes*, migratory grasshopper, *Hylemya platura*, seed-corn maggot, *Agromyza parvicornis*, corn blotch leafminer, *Anaphothrips obscurus*, grass thrips, *Solenopsis milesta*, thief ant, and *Tetranychus urticae*, two-spotted spider mite using techniques well known in the art. Those transgenic maize plants having insecticidal properties are then subjected to field trials.

Example 8

Wheat Bioassays

Wheat plants demonstrated to contain the peroxidase coding sequence by Southern analysis or PCR are evaluated for insecticidal activity against *Pseudaletia unipunctata*, army worm; *Spodoptera frugiperda*, fall armyworm; *Elasmopalpus lignosellus*, lesser cornstalk borer; *Agrotis orthogonia*, pale western cutworm; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; or *Aceria tulipae*, wheat curl mite, using techniques well known in the art. Those transgenic wheat plants having insecticidal properties are subjected to field trials.

Example 9

Sorghum Bioassays

Sorghum plants demonstrated to contain the peroxidase coding sequence by Southern analysis or PCR are evaluated for insecticidal activity against *Chilo partellus*, sorghum borer; *Spodoptera frugiperda*, fall armyworm; *Helicoverpa zea*, corn earworm; Elasmopalpus lignosellus, lesser cornstalk borer; Feltia subterranean granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Contarinia sorghicola*, sorghum midge; *Tetranychus cinnabarinus*, carmine spider mite; or *Tetranyches urticae*, twospotted spider mite, using

Example 10
Rice Bioassays

Rice plants demonstrated to contain the peroxidase coding sequence by Southern analysis or PCR are evaluated for insecticidal activity against *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; or *Acrosternum hilare*, green stink bug, using methods well known in the art. Those transgenic rice plants having insecticidal properties are subjected to field trials.

Example 11
Barley Bioassays

Barley plants demonstrated to contain the peroxidase coding sequence by Southern analysis or PCR are evaluated for insecticidal activity against *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servos*, brown stink bug; *Hylemya platura*, seedcorn maggot; *Mayetiola destructor*, Hessian fly; Thysanoptera, Thrips; or *Petrobia latens*, brown wheat mite using methods well known in the art. Those transgenic barley plants having insecticidal properties are subjected to field trials.

D. Breeding and Seed Production

Example 12
Breeding

The plants obtained via tranformation with a nucleic acid sequence of the present invention can be any of a wide variety of plant species, including those of monocots and dicots; however, the plants used in the method of the invention are preferably selected from the list of agronomically important target crops set forth supra. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, N.Y. (1981); Crop Breeding, Wood D. R. (Ed.) American Society of Agronomy Madison, Wisconsin (1983); Mayo O., The Theory of Plant Breeding, Second Edition, Clarendon Press, Oxford (1987); Singh, D. P., Breeding for Resistance to Diseases and Insect Pests, Springer-Verlag, N.Y. (1986); and Wricke and Weber, Quantitative Genetics and Selection Plant Breeding, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pestidice treatment or allow one to dispense with said methods due to their modified genetic properties. Alternatively new crops with improved stress tolerance can be obtained, which, due to their optimized genetic "equipment", yield harvested product of better quality than products that were not able to tolerate comparable adverse developmental conditions.

Example 13
Seed Production

In seed production, germination quality and uniformity of seeds are essential product characteristics, whereas germin ati on quality an d uniformity of seeds harvested and sold by the farmer is not important. As it is difficult to keep a crop free from other crop and weed seeds, to control seedborne diseases, and to prod uce seed with good germination, fairly ex ten sive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (Apron®), and pirimiphos-methyl (Actellic®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods, such as the methods examplified above, which are characterized by the use of transgenic plants, transgenic plant material, or transgenic seed according to the present invention.

The seeds may be provided in a bag, container or vessel comprised of a suitable packaging material, the bag or container capable of being closed to contain seeds. The bag, container or vessel may be designed for either short term or long term storage, or both, of the seed. Examples of a suitable packaging material include paper, such as kraft paper, rigid or pliable plastic or other polymeric material, glass or metal. Desirably the bag, container, or vessel is comprised of a plurality of layers of packaging materials, of the same or differing type. In one embodiment the bag, container or vessel is provided so as to exclude or limit water and moisture from contacting the seed. In one example, the bag, container or vessel is sealed, for example heat sealed, to prevent water or moisture from entering. In another embodiment water absorbent materials are placed between or adjacent to packaging material layers. In yet another embodiment the bag, container or vessel, or packaging material of which it is comprised is treated to limit, suppress or prevent disease, contamination or other adverse affects of storage or transport of the seed. An example of such treatment is sterilization, for example by chemical means or by exposure to radiation. Comprised by the present invention is a commercial bag comprising seed of a transgenic plant comprising a gene of the present invention that is expressed in said transformed plant at higher levels than in a wild type plant, together with a suitable carrier, together with label instructions for the use thereof for conferring broad spectrum disease resistance to plants.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

What is claimed is:

1. An isolated nucleic acid molecule comprising SEQ ID NO:3.

2. A chimeric construct comprising a heterologous promoter sequence operatively linked to the nucleic acid molecule of claim 1.

3. A recombinant vector comprising the chimeric construct of claim 2.

4. A plant cell comprising the chimeric construct of claim 2.

5. A plant comprising the plant cell of claim 4.

6. A plant according to claim 5, wherein said plant is maize.

7. Seed from the plant according to claim 5.

8. A method of producing an insect-resistant plant, comprising introducing a nucleic acid molecule according to claim 1 into said plant, wherein said nucleic acid molecule is expressible in said plant in an effective amount to control an insect.

9. The method of claim 8, wherein the insect is *Ostrinia nubilalis, Heliothis zea*, or *Spodoptera frugiperda*.

10. The method of claim 8, wherein said plant is maize.

* * * * *